United States Patent [19]
Guy et al.

[11] Patent Number: 5,334,164
[45] Date of Patent: Aug. 2, 1994

[54] VARIABLE INTERIOR DIMENSION CANNULA ASSEMBLY

[75] Inventors: Thomas D. Guy, Fairfield; Alex Ianniruberto, Waterbury, both of Conn.

[73] Assignee: United States Surgical Corporation, Norwalk, Conn.

[21] Appl. No.: 816,215

[22] Filed: Jan. 3, 1992

[51] Int. Cl.$^5$ ............................................. A61M 5/00
[52] U.S. Cl. ..................................... 604/248; 604/246
[58] Field of Search ........ 604/165, 274, 158, 164–165, 604/169, 272–274, 246–248, 256; 251/4

[56] References Cited

U.S. PATENT DOCUMENTS

| | | |
|---|---|---|
| 2,416,391 | 2/1947 | Hixson ................................. 251/4 |
| 2,569,850 | 10/1951 | Falcom ................................ 251/4 |
| 3,086,797 | 4/1963 | Webb . |
| 3,197,173 | 7/1965 | Taubenheim . |
| 3,329,390 | 7/1967 | Hulsey ................................ 251/4 |
| 3,875,938 | 4/1975 | Mellor . |
| 3,989,049 | 11/1976 | Yoon . |
| 3,994,287 | 11/1976 | Turp et al. . |
| 4,000,739 | 1/1977 | Stevens . |
| 4,177,814 | 12/1979 | Knepshield et al. . |
| 4,233,982 | 11/1980 | Bauer et al. . |
| 4,240,411 | 12/1980 | Hosono . |
| 4,338,934 | 7/1982 | Spademan . |
| 4,379,458 | 4/1983 | Bauer et al. . |
| 4,424,833 | 1/1984 | Spector et al. . |
| 4,430,081 | 2/1984 | Timmermans . |
| 4,512,766 | 4/1985 | Vailancourt . |
| 4,531,937 | 7/1985 | Yates . |
| 4,535,773 | 8/1985 | Yoon . |
| 4,540,411 | 9/1985 | Bodicky ........................ 604/169 |
| 4,580,573 | 4/1986 | Quinn . |
| 4,601,710 | 7/1986 | Moll . |
| 4,610,665 | 9/1986 | Matsumoto et al. . |
| 4,610,674 | 9/1986 | Suzuki et al. . |
| 4,611,785 | 9/1986 | Steer . |
| 4,626,245 | 12/1986 | Weinstein . |
| 4,629,450 | 12/1986 | Suzuki et al. . |
| 4,634,432 | 1/1987 | Kocak . |
| 4,654,030 | 3/1987 | Moll et al. . |
| 4,655,752 | 4/1987 | Honkanen et al. . |
| 4,673,393 | 6/1987 | Suzuki et al. . |

(List continued on next page.)

FOREIGN PATENT DOCUMENTS

| | | |
|---|---|---|
| 29864 | 6/1981 | European Pat. Off. . |
| 344907 | 12/1989 | European Pat. Off. . |
| 350291 | 1/1990 | European Pat. Off. . |
| 2845643 | 4/1980 | Fed. Rep. of Germany . |
| 3042229 | 11/1980 | Fed. Rep. of Germany . |
| 3324699 | 12/1984 | Fed. Rep. of Germany . |
| 1221730 | 6/1960 | France . |
| 1199498 | 7/1970 | United Kingdom . |
| 2019219 | 10/1979 | United Kingdom . |
| 2063679 | 6/1981 | United Kingdom . |

OTHER PUBLICATIONS

European Patent Application Pub. No. 0 045 668 A1.
PCT International Application Pub. No. WO 92/11880.
European Search Report EP 92 12 2149.

*Primary Examiner*—C. Fred Rosenbaum
*Assistant Examiner*—Manuel Mendez

[57] ABSTRACT

A cannula assembly for use in conjunction with endoscopic surgical techniques includes a cannula, a housing mounted on one end of the cannula, and a variable interior dimension cannula valve assembly in the housing. The variable interior dimension cannula valve assembly includes a flexible tubular member having a distal portion affixed to the housing, an intermediate portion capable of changing interior dimension and a proximate portion including a rigid rotating means and a locking means. The interior dimension of the cannula valve assembly may be set to a desired size to fit a surgical instrument inserted into the cannula passage while maintaining a substantially air-tight seal.

18 Claims, 7 Drawing Sheets

U.S. PATENT DOCUMENTS

| | | |
|---|---|---|
| 4,705,511 | 11/1987 | Kocak . |
| 4,798,594 | 1/1989 | Hillstead . |
| 4,804,375 | 2/1989 | Robertson ............................. 251/4 |
| 4,813,938 | 3/1989 | Raulerson . |
| 4,842,591 | 6/1989 | Luther . |
| 4,857,062 | 8/1989 | Russell . |
| 4,874,377 | 10/1989 | Newgard et al. . |
| 4,895,346 | 1/1990 | Steigerwald . |
| 4,909,798 | 3/1990 | Fleischhacker et al. . |
| 4,917,668 | 4/1990 | Haindl . |
| 4,929,235 | 5/1990 | Merry et al. . |
| 4,935,010 | 6/1990 | Cox et al. . |
| 4,960,412 | 10/1990 | Fink . |
| 4,966,588 | 10/1990 | Rayman et al. . |
| 4,978,341 | 12/1990 | Niederhauser . |
| 5,000,745 | 3/1991 | Guest et al. . |
| 5,006,114 | 4/1991 | Rogers et al. . |
| 5,009,391 | 4/1991 | Steigerwald . |
| 5,158,553 | 10/1992 | Berry et al. ......................... 604/248 |
| 5,197,955 | 3/1993 | Stephens et al. .................... 604/167 |
| 5,203,774 | 4/1993 | Gilson et al. ........................ 604/165 |

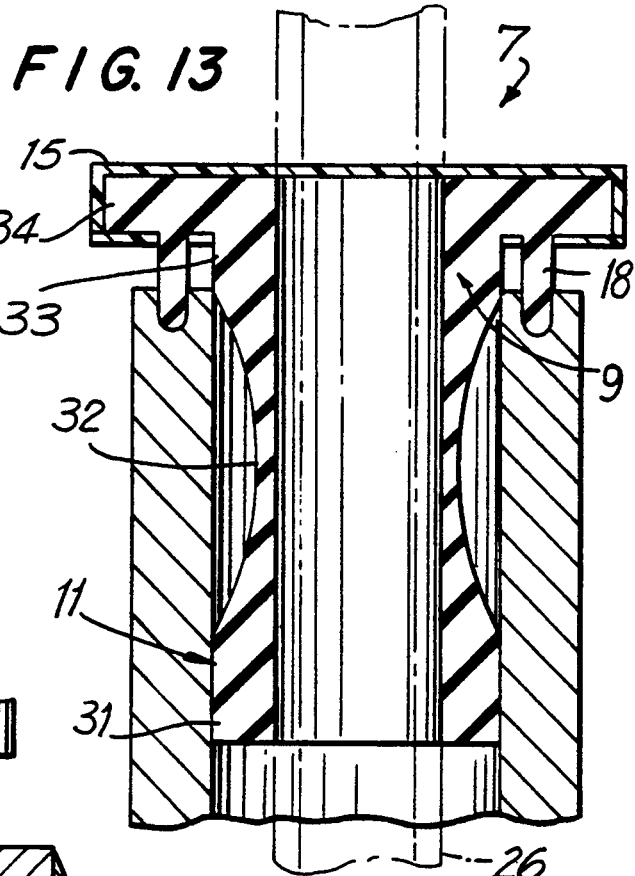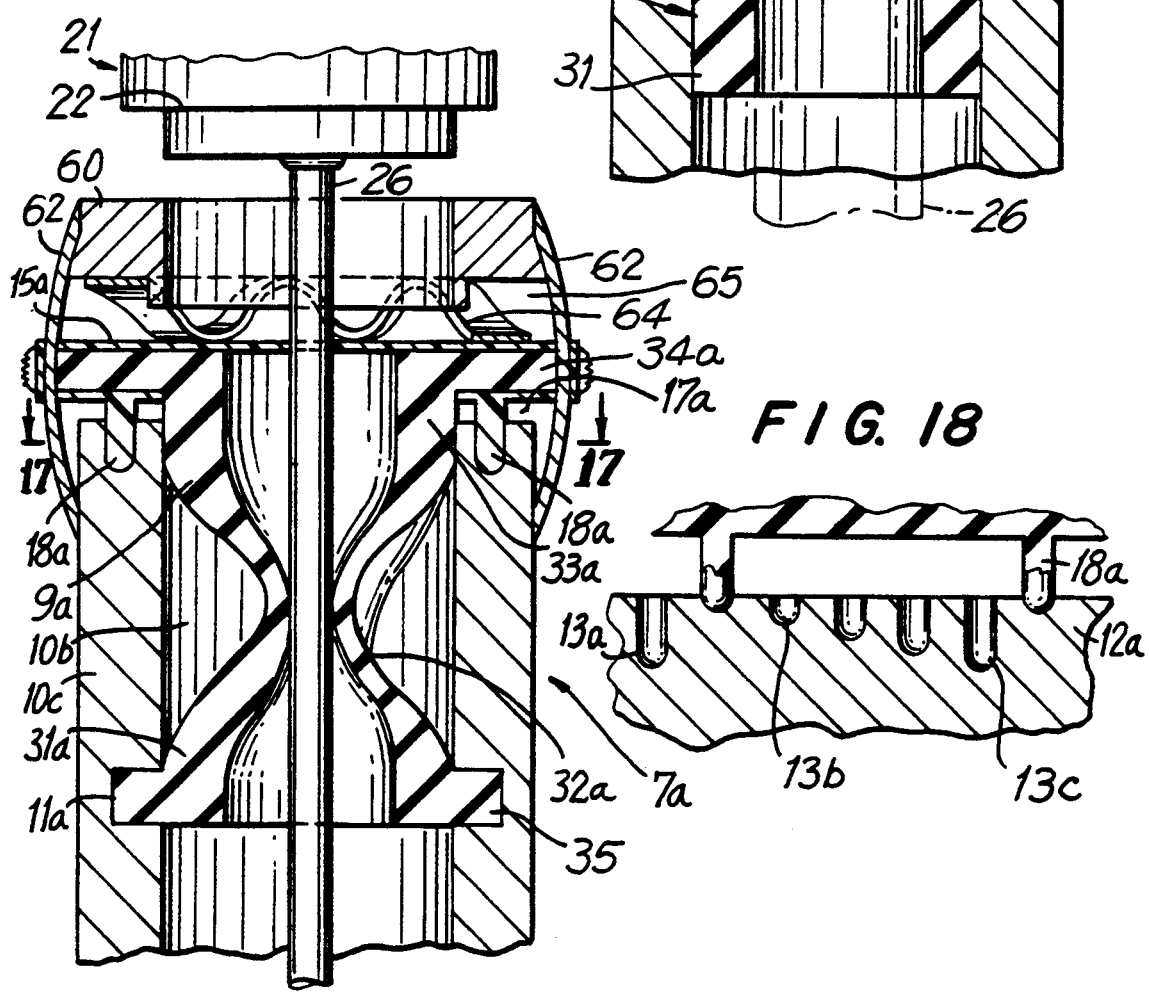

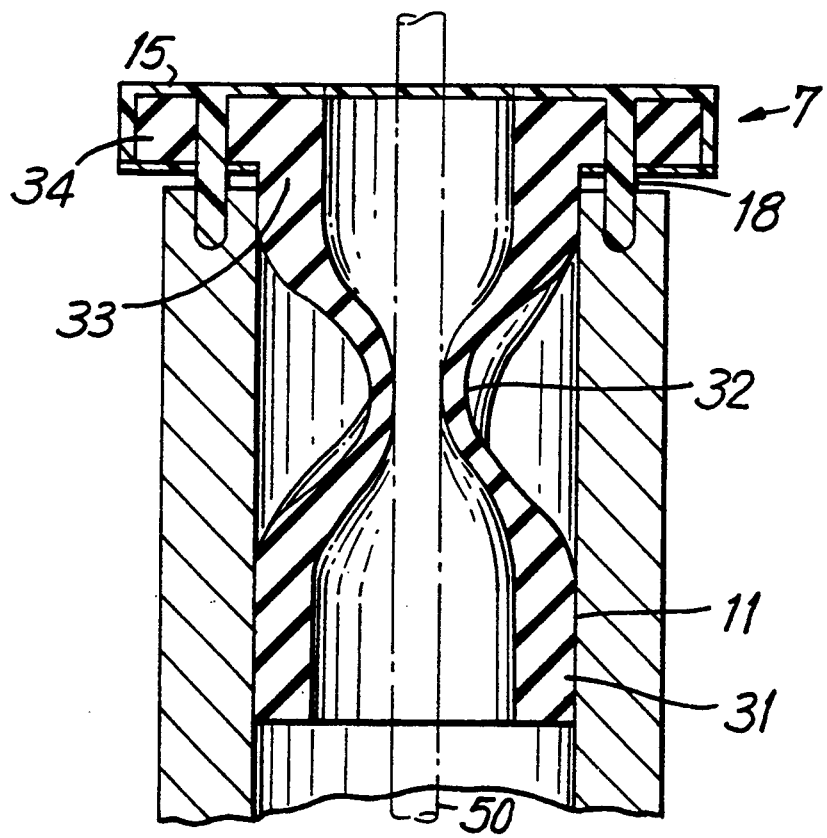
FIG. 14
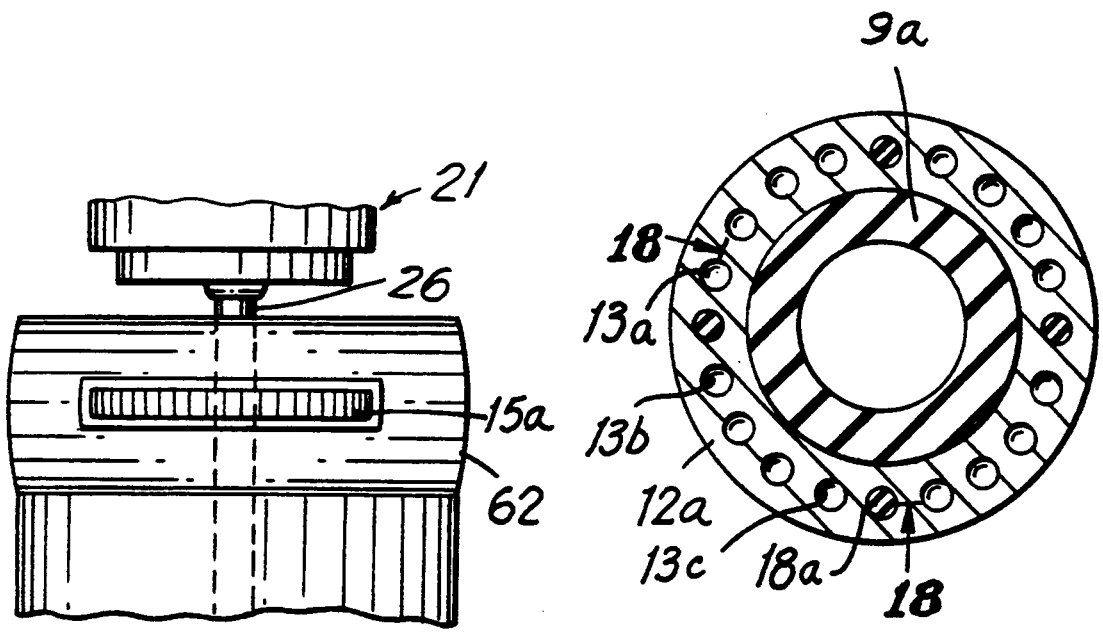
FIG. 16
FIG. 17

VARIABLE INTERIOR DIMENSION CANNULA ASSEMBLY

FIELD OF THE INVENTION

The present invention relates to cannula assemblies adapted to receive trocars, endoscopes or other surgical instruments for use in conjunction with insufflatory surgery, and more particularly relates to cannulas having variable interior dimension which allow receipt of surgical instruments having different diameters.

DESCRIPTION OF THE BACKGROUND ART

Insufflatory surgery involves filling a body cavity with pressurized gas to maintain the cavity under a certain predetermined pressure. Such surgery may be performed by first puncturing the skin of a desired body cavity region with a needle. Insufflation gas is then introduced into the body cavity to inflate the cavity via a stylet in the needle.

A trocar is then used to puncture the body cavity. The trocar is inserted through a cannula or sheath, which cannula partially enters the body cavity through the incision made by the trocar. The trocar may then be removed from the cannula, and an elongated endoscope may be inserted through the cannula to view the anatomical cavity.

Various types of cannula or trocar assemblies are provided with valves so that when the trocar or other surgical instrument is removed from or inserted into the cannula a relatively constant or certain pressure is maintained within the body cavity.

For example, U.S. Pat. Nos. 4,601,710 to Moll and 4,654,030 to Moll et al. disclose trocar assemblies which include an elongate trocar obturator having a piercing tip at its front end and an elongate trocar tube or cannula in which the trocar obturator is housed. As shown in the '030 patent, a flapper valve may be employed to close off the cannula passage after the trocar obturator or other instrument has been withdrawn.

A gasket may also be employed to ensure a seal between the trocar assembly and an instrument inserted therein. U.S. Pat. No. 4,000,739 to Stevens, for example, teaches a hemostasis cannula having a pair of juxtaposed gaskets mounted in the passageway to the cannula, the first having a round hole and the second a Y-shaped slit. U.S. Pat. No. 3,994,287 to Turp et al. describes a trocar assembly which includes a flexible insulating ring received in a flange and a collar which retains the flexible ring in the flange. The flexible ring is allowed to flex as an instrument is inserted into the cannula and provides a seal with the instrument to prevent gas leakage.

Endoscopic surgical procedures employ a variety of surgical instruments, e.g., endoscopes, biopsy forceps, bipolar forceps, coagulation probes, etc. Due to the relatively noninvasive nature of endoscopic procedures, endoscopy is a preferred surgical approach when possible. As such, additional instruments and accessories for use in endoscopic procedures are being introduced at a rapid pace. These instruments have differing sizes, for example, some instruments have a cross-sectional diameter in their elongate regions on the order of 5 mm whereas others have a diameter of 10 mm or larger. In recognition of this instrument variability, cannulas are available in different inner diameters. Commercially available trocars offer cannulas having a broad range of inner diameters, ranging from 3 to 12 mms (e.g., 3, 5, 7, 8, 10, 11 and 12 mm sizes).

Despite the availability of trocar assemblies having cannulas of various sizes, it is both inconvenient and impractical for a surgeon to insert multiple cannulas into a patient to accommodate the various instrument sizes employed in a given surgical procedure. This greatly restricts the flexibility available to surgeons in performing endoscopic procedures. For example, the use of a 5 mm instrument in a 10 mm cannula is not possible because a gas seal would not exist between the trocar assembly and the instrument. Similarly, the use of a 10 mm instrument in a 5 mm cannula is impossible because the instrument simply doesn't fit. It has therefore been necessary heretofore for a surgeon to effect multiple cannula placements or to employ accessory devices having a predetermined aperture diameter to accommodate the use of instruments of varying sizes. Consequently, such multiple placement dictates multiple invasionary punctures into the body of a patient and the use of accessory devices can be a clinical nuisance. It is desirable to decrease the number of punctures because, e.g., the possibility of infection would be decreased, patient discomfort would be decreased and both time and money would be saved, while accommodating instruments of varying diameters.

OBJECTS AND SUMMARY OF THE INVENTION

It is an object of the present invention to provide a variable interior dimension cannula for an insufflation trocar assembly which minimizes leakage through the cannula while an obturator or other surgical instrument is inserted in said cannula.

It is another object of the present invention to provide an insufflation cannula assembly which can receive obturators or other surgical instruments having a range of different outside diameters.

It is a further object of the present invention to provide an insufflation cannula assembly which has means for varying the interior dimension of the cannula to correspond to the outside diameter of an obturator or other surgical instrument allowing for the use of several different sized instruments in a single cannula assembly.

It is yet another object of the present invention to provide an insufflation cannula assembly for use with an obturator, endoscope or other surgical instrument, which cannula assembly provides negligible or no gas leakage.

It is yet a further object of the present invention to reduce the number of invasionary punctures necessary during the course of a surgical procedure.

In one form of the present invention, a cannula assembly for use in conjunction with endoscopic surgical techniques includes a variable dimension valve mounted within the cannula. The variable dimension valve is adapted to receive surgical instruments having different diameters while maintaining a substantially air-tight seal between the interior of the cannula and any of the surgical instruments used in conjunction with the cannula.

The variable dimension valve includes a tubular member having first and second end portions and an intermediate portion between the two end portions. Upon application of torsional force to one or both of the ends, the intermediate portion constricts or expands, thus reducing or increasing the interior dimension of the intermediate portion. The torsional force can be increased and the interior dimension of the valve is reduced until an airtight seal is formed against the surgical instrument. The interior dimension of the valve can be reduced to form an airtight seal on itself even in the absence of a surgical instrument inserted therethrough.

The variable dimension valve may be mounted to the interior passage of the cannula by having one end portion of the valve fixedly attached to the interior passage and the other end portion fixedly attached to a rigid rotating means. Thus, when the rotating means is activated, the interior dimension of the valve can be made to constrict or expand as one of the end portions is rotated.

The variable dimension valve may be fixedly mounted in the cannula's interior passage and co-axial with the cannula's opening using any known means, e.g., friction, mechanical devices, or adhesives. The other end portion of the valve may be mounted to the rotating means in similar fashion. The rotating means is provided with a means for fixing the position of the valve's end portions in place to allow for maintenance of a desired valve interior dimension.

Preferred forms of the variable interior dimension valve assembly, as well as other embodiments, objects, features and advantages of this invention, will be apparent from the following detailed description of illustrative embodiments thereof, which is to be read in connection with the accompanying drawings.

BRIEF DESCRIPTION OF THE DRAWINGS

FIG. 13 is a partial view of a variable dimension valve mounted inside a cannula assembly.

FIG. 14 is a partial view of the variable dimension valve shown in FIG. 13 in a reduced interior dimension position sealing against a surgical instrument having an exterior diameter smaller than the maximum interior dimension of the cannula assembly.

FIG. 15 is a partial view of another embodiment of a variable dimension valve mounted inside a cannula assembly according to the present invention.

FIG. 16 is a partial exterior view of the variable dimension valve and cannula assembly shown in FIG. 15.

FIG. 17 is a transverse cross-sectional view of the variable dimension valve shown in FIG. 15, taken along line 17—17 of FIG. 15.

FIG. 18 is a sectional view of the transverse cross-sectional view of the variable dimension valve shown in FIG. 17, taken along lines 18—18 of FIG. 17.

DETAILED DESCRIPTION OF THE INVENTION

Figure 1:
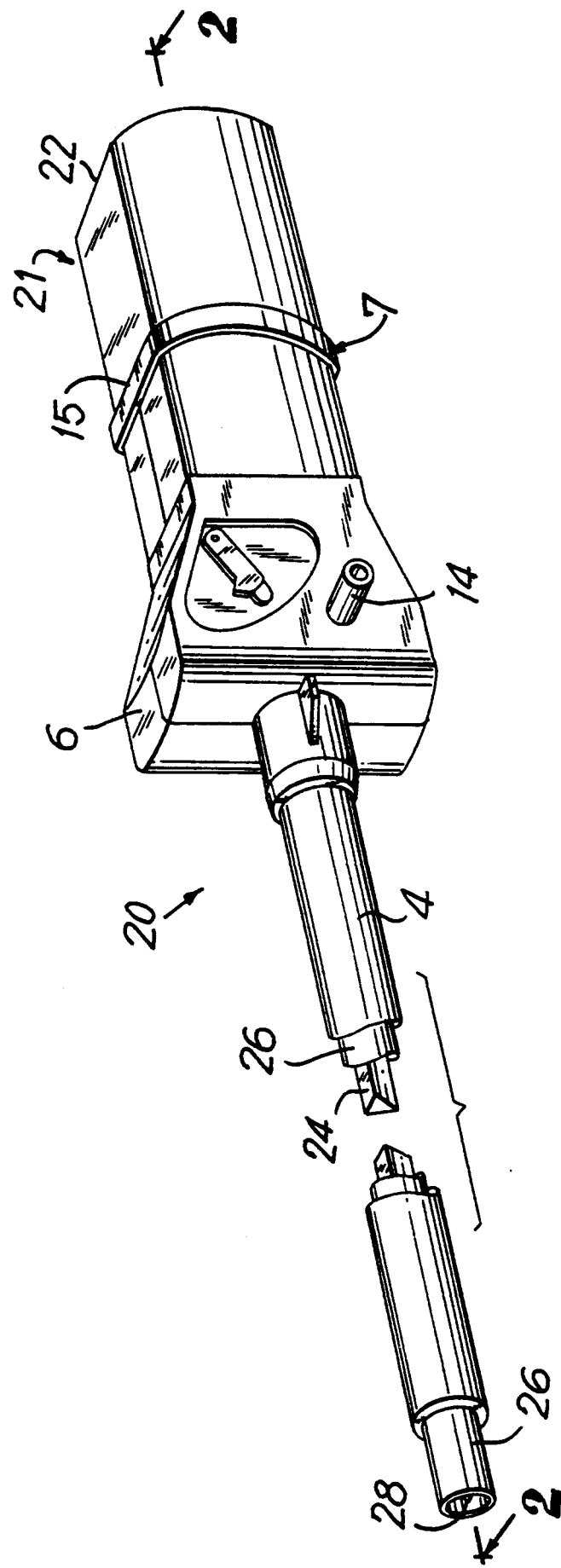
FIG. 1 is an isometric view of a trocar assembly according to the present invention with an obturator assembly mounted thereon.
Figure 2:
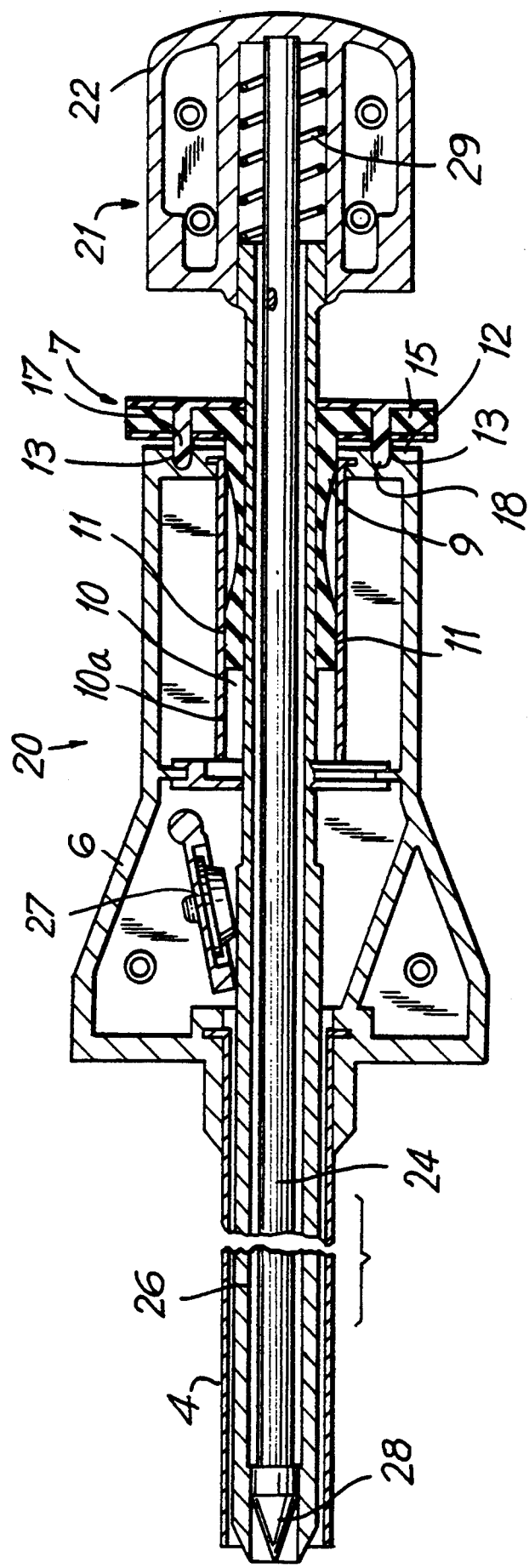
FIG. 2 is a sectional view of the trocar assembly and obturator assembly shown in FIG. 1, taken along line 2—2 of FIG. 1.

Referring initially to FIGS. 1 and 2 of the drawings, it will be seen that an illustrative trocar assembly 20 used in connection with insufflatory surgical techniques according to the present invention basically includes a cannula tube 4, a housing 6 mounted on one end of the cannula tube 4, and a variable interior dimension cannula valve assembly 7 mounted on the housing 6 opposite and co-axially with cannula tube 4. The cannula tube 4 is formed as an elongated sleeve having opposite proximate and distal open ends, and thus defines a cannula passage 8 in its interior. The cannula tube 4 may be formed from a stainless steel, fiberglass or other rigid material known to those with skill in the art.

The housing 6 of the trocar assembly 20 is rigidly secured to the proximate end of the cannula tube 4. The housing 6 has an open interior for mounting other components of the cannula assembly, and has a valve compartment 10 defined, at its proximate end, by a circular plate 12 and walls 10a, which valve compartment 10 is situated co-axially with the cannula tube 4. An O-ring (not shown) may be mounted on the cannula tube 4 to prevent leakage between the cannula tube 4 and the housing 6. Additionally, the housing 6 includes a stopcock port 14 into which the nozzle of a stopcock (not shown) is inserted, the port 14 being provided for passing additional insufflating gas into a body cavity when indicated.

The variable interior dimension cannula valve assembly 7 basically includes a flexible tubular member 9 rigidly attached to the valve compartment 10 generally at point 11 and a rigid rotating means 15 having locking means 17. The locking means 17 is shown in FIG. 2 as a pin 18 and detent pin receiving means 13. The locking means 17 may incorporate a pinwheel device which mounts to the rotating means 15, which pinwheel device communicates with detents 13 disposed in the circular plate 12. The detents 13 can be placed at fixed intervals which correspond to fixed diametral gradations, thus facilitating a secure fit around surgical instruments having known diameters which are contained within the valve assembly 7. In practice, a surgeon turns the rotating means 15 and, when the desired dimension is achieved, pushes down on the rotating means 15 thus pushing the pins 18 of the pinwheel into the pin receiving means 13 to achieve a locked dimension.

Figure 3:
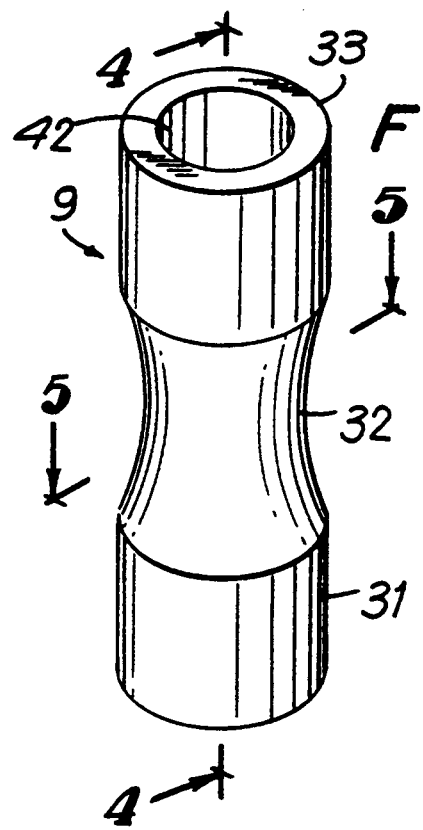
FIG. 3 is an isometric view of one embodiment of a variable dimension valve according to the present invention.
Figure 4:
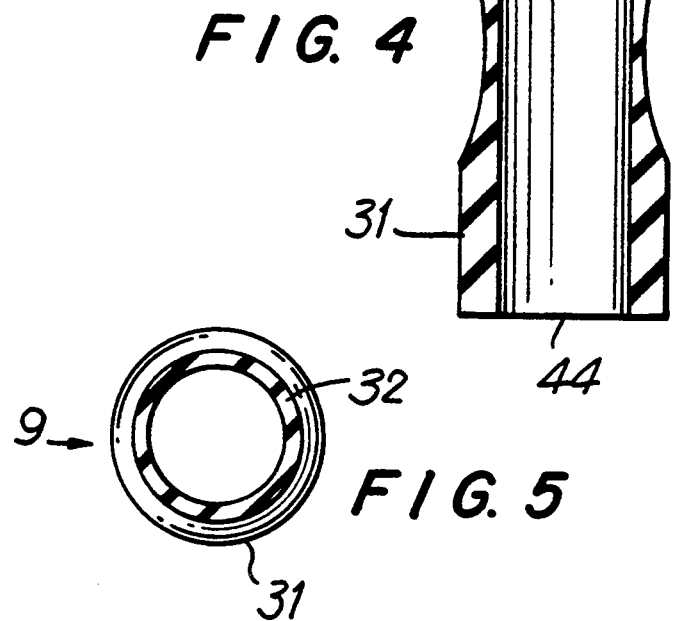
FIG. 4 is a sectional view of the variable dimension valve shown in FIG. 3, taken along line 4—4 of FIG. 3.
Figure 5:
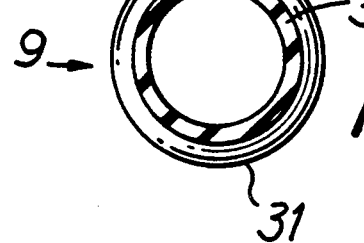
FIG. 5 is a sectional view of the variable dimension valve shown in FIG. 3, taken along line 5—5 of FIG. 3.
Figure 6:
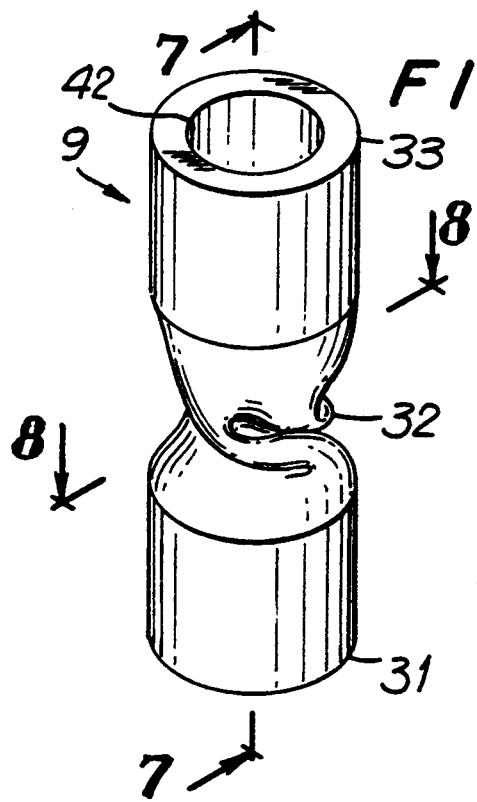
FIG. 6 is an isometric view of the variable dimension valve shown in FIG. 3, further depicting the valve after a torsional force has been applied.
Figure 8:
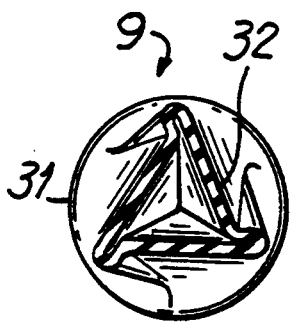
FIG. 8 is a sectional view of the variable dimension valve shown in FIG. 6, taken along line 8—8 of FIG. 6.
Figure 7:
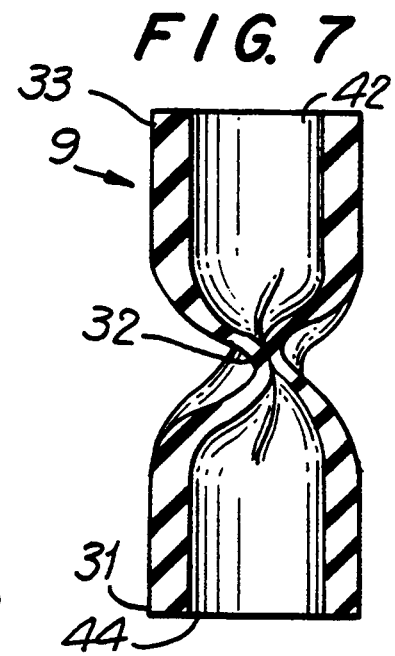
FIG. 7 is a sectional view of the variable dimension valve shown in FIG. 6, taken along line 7—7 of FIG. 6.

The variable interior dimension cannula valve assembly 7 has a proximate opening 42 and distal opening 44 (see FIG. 4), both openings being situated co-axially with the cannula tube 4. Applying torsional force by rotating the variable interior dimension cannula valve assembly 7 via rotating means 15, causes the intermediate portion 32 to twist and, consequently, the interior dimension of the intermediate portion 32 (see FIGS. 3 through 7) to change. The tube 9 can range from being open, as shown in FIGS. 3 through 5, to being closed and air-tight, as shown in FIGS. 6 through 8. As can be seen in FIGS. 3 through 5, when the tube 9 is wide open, a substantially circular aperture is provided by the valve. When torsional force is applied, the interior walls of the tube 9 move inward and toward one another and a collapsing polygonal aperture is formed. When the torsional force causes the interior walls of the tube 9 to collapse such that the polygonal aperture is completely closed, (as in shown in FIGS. 6 through 8), the walls of the tube intersect at the central axis of the tube. In the embodiment depicted in FIGS. 6 through 8, the polygonal aperture is substantially triangular and the lines of intersection (formed by the intersecting walls) are equidistant, radiating outwardly from the central axis at approximately 120° angles. As above, the locking means 17 may be engaged to maintain a selected interior dimension.

The trocar assembly 20, with its cannula tube 4, housing 6 and variable interior dimension cannula valve assembly 7, is adapted to receive a surgical instrument through the valve assembly 7. An example of such an instrument is the obturator 21 shown in FIGS. 1 and 2 of the drawings.

The obturator 21 includes a hand grip portion or head 22, a shaft 24 mounted to the head 22 of the obturator 21 and extending outwardly from the head 22, and an obturator shield 26 which houses the shaft 24 and covers a piercing tip 28 for puncturing the body cavity. A spring 29 in the head 22 of the obturator 21 biases the shield 26 axially away from the head 22 so that it covers the obturator tip 28.

The obturator 21 is mounted on the trocar assembly 20 so that the shaft 24 and shield 26 are slidably received in the cannula passage 8 with the obturator shield 26 extending beyond the distal end of the cannula tube 4.

In operation, the distal end of the trocar assembly 20 is placed against the skin at the body cavity region, and pressure is exerted on the head 22 of the obturator 21 thereby causing pressure against the skin. This pressure causes the obturator shield 26 to be pushed rearwardly against the force of the spring 29 to a retracted position, thereby exposing the piercing tip 28 of the obturator 21. The tip 28 enters the skin and underlying tissue with continued pressure. Once the tip 28 has penetrated the tissue and entered the cavity, the force against the distal end of the shield 26 ceases and the shield is automatically moved axially forward to its extended position covering the tip 28 through the action of the spring 29.

A more detailed description of a trocar assembly and its operation is provided in Moll et al. U.S. Pat. No. 4,654,030, which is incorporated herein by reference.

As shown in FIG. 2, the trocar assembly 20 of the present invention may include a flapper valve 27 which opens to allow a surgical instrument, such as the obturator 21, to be inserted through the cannula tube 4, and closes when the surgical instrument has been withdrawn, thus maintaining gas pressure in the body cavity which has been inflated with an insufflation gas.

Basically, the flapper valve 27 includes three components: a valve seat, a valve plug which engages the valve seat, and a mechanism for mounting the valve plug and for pivoting the plug into and out of engagement with the valve seat.

A more detailed description of the flapper valve assembly described herein, and its operation, is provided in Lander, U.S. Pat. No. 4,943,280, which is incorporated herein by reference. The ability of the valve, according to the present invention, to seal itself completely, renders the presence of the flapper valve optional.

When the tubular member 9 is used in conjunction with a locking means 17 having a pin and detent assembly, a flange 34 is affixed to the proximate portion 33 of the tubular member 9. Holes 46 in the flange 34 allow any pins 18 to pass through and engage detents 13 located on the circular plate 12 of the valve compartment 10.

In accordance with the present invention, and as shown in FIGS. 13 and 14 of the drawings, the variable interior dimension cannula valve assembly 7, includes a flexible tubular member 9, having a distal portion 31, an intermediate portion 32, and a proximate portion 33 which includes flange portion 34, and holes 46 (see FIG. 9), as well as rotating means 15, and locking means 17 having pins 18 and detent pin receiving means 13. In practice, the pins 18 are affixed to the rotating means 15 and pass through the holes 46 in the flange 34 and engage the receiving means 13 of circular plate 12, thereby maintaining the predetermined interior dimension of the cannula valve assembly 7. The outside surface of the distal portion 31 is affixed to the interior surface of the walls 10a of the valve compartment 10 at interface 11. The proximate portion 33 of the tubular member 9 is rigidly affixed to the rotating means 15 via the flange 34 and has pins 18 passing through which engage the receiving means 13 positioned in the circular plate 12 or, alternatively, the receiving means 13 positioned in the proximate portion of the housing 6.

Figure 9:
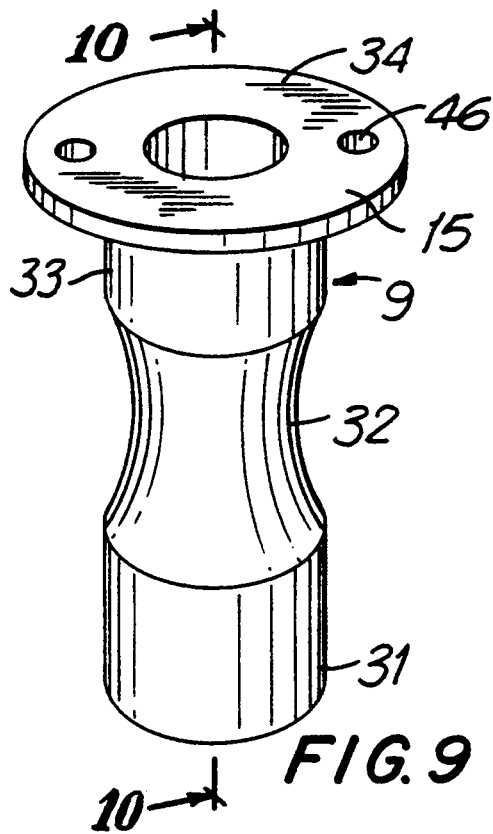
FIG. 9 is an isometric view of another embodiment of a variable dimension valve according to the present invention.
Figure 10:
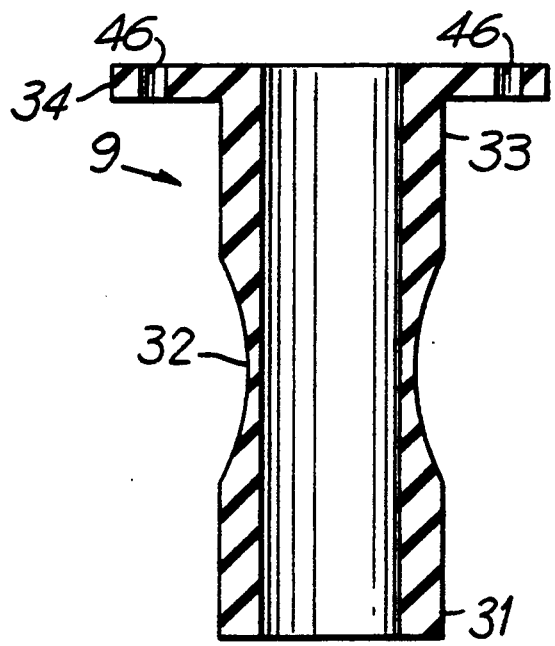
FIG. 10 is a sectional view of the variable dimension valve shown in FIG. 9, taken along line 10—10 of FIG. 9.
Figure 11:
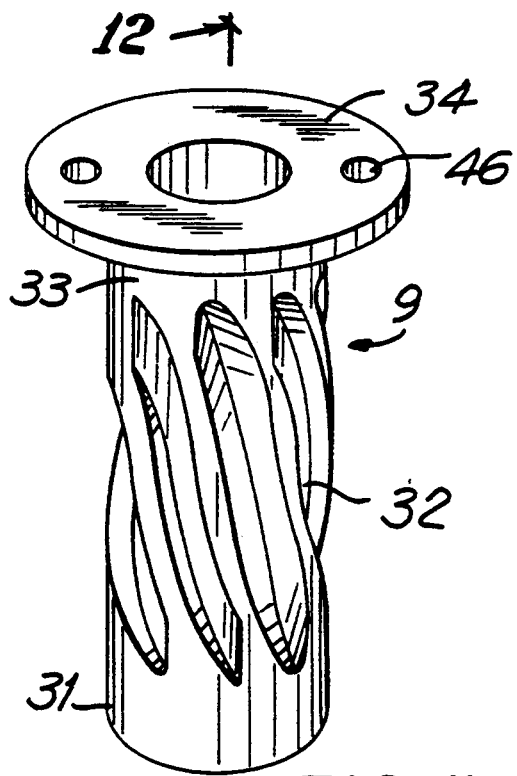
FIG. 11 is an isometric view of another embodiment of a variable dimension valve according to the present invention.
Figure 12:
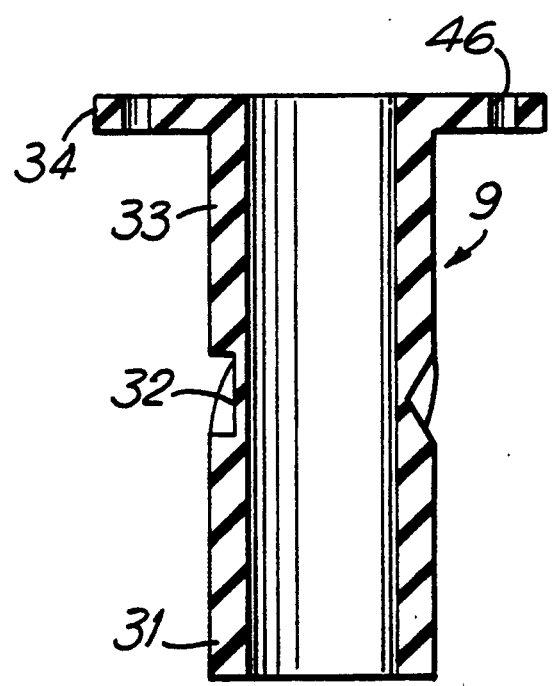
FIG. 12 is a sectional view of the variable dimension valve shown in FIG. 11, taken along line 12—12 of FIG. 11.

The intermediate portion 32 of flexible tubular member 9 is designed to change interior dimension when torsional force is applied and portions 31 and 33 are rotated in relation to one another while the interior diameter of portions 31 and 33 remains substantially unchanged. FIGS. 9 through 12 depict two embodiments of the tubular member 9 and formations of the intermediate portion 32 to allow for the interior dimension changes described above. In one embodiment, the intermediate portion 32 of the tubular member 9 includes a smooth concave outer wall as depicted in FIG. 9 and further depicted in cross-section in FIG. 10. In the absence of any torsional force, the interior dimension of the tubular member 9 is substantially uniform. In FIG. 11, the intermediate portion 32 of the tubular member 9 is depicted as being fluted, with the flutes being disposed in a generally helical direction. The tubular member of FIG. 11 is shown in cross-section in FIG. 12. It will be appreciated that any method or design known in the appropriate art may be utilized to provide the necessary flexibility of intermediate portion 32.

The flexible tubular member 9 may be made of any material which will allow for a variable interior dimension by rotating the ends of the tube 9 in relation to one another. Suitable materials include, for example, natural rubber, synthetic rubbers and elastomeric latexes. TYGON ™ for example, may be used.

The rigid rotating means 15 may be made of metal, nylon, rigid polyurethane, or other plastics. Further, it may be made of the same or different material than that of the housing.

The distal portion 31 of flexible tubular member 9 may be rigidly affixed to the walls 10a of the valve compartment 10 at interface 11 by any means known in the appropriate art, including, for example, by friction, adhesively or mechanically. The means need only ensure that rotation of proximate portion 33 does not allow movement of distal portion 31. The composition, shape and size of flexible tubular member 9 is not critical as long as the tubular member 9 fits into, and can be rigidly affixed to the valve compartment 10, has an opening large enough to accept the desired surgical instruments and whose intermediate portion 32 changes interior dimension upon rotation of opposing ends 31 and 33.

Rigid rotating means 15 and pin(s) 18 may be formed as a single unit in conjunction with the flange 34 or as separate units and they may be of the same or different materials. They may be of any composition and size as is appropriate for flexible tube member 9 and valve compartment 10. While the locking means 17 illustrated in FIGS. 2, 13 and 14 of the drawings are such that the pin 18 physically enters receiving means 13, friction between valve compartment 10 and rotating means 15 and flange 34 may also be used where the composition of the walls 10a of the valve compartment 10 and rotating means 15 and flange 34 provide the necessary coefficient of friction to maintain the desired orientation of rotating means 15 to thereby provide and maintain whatever interior dimension is desired of the intermediate portion 32.

By way of illustration, FIG. 13 shows an obturator shield 26 having an exterior diameter of the size of the maximum interior dimension of the flexible tubular member 9 passing through the variable interior dimension cannula valve assembly 7. FIG. 14 shows the same variable interior dimension cannula valve assembly 7 with the interior dimension of the flexible tubular member 9 reduced to seal around the shaft of a surgical instrument 50 having an exterior diameter smaller than the maximum interior dimension of the flexible tubular member 9, thus ensuring an effective seal.

In an alternative embodiment shown in FIG. 15, locking means 17a incorporates spring means 64 which forces pins 18a securely into detent pin receiving means 13a. More particularly, this variable interior dimension valve assembly 7a includes a tubular member 9a having a distal portion 31a, an intermediate portion 32a having at least a portion that is flexible and/or resilient, and a proximate portion 33a having a proximate flange portion 34a. The distal portion 31a also includes a distal flange portion 35. The tubular member 9a is housed in valve compartment 10b at point of attachment 11a on wall 10c where the distal flange portion 35 is attached by an adhesive or such other means that are known to those with skill in the art. The spring means 64 is located in a spring means compartment 65 above rigid rotating means 15a. The rigid rotating means 15a covers the proximate flange portion 34a and has the pins 18a secured to its distal-most portion. The pins 18a project in the direction of circular plate 12a.

The spring means compartment 65 is defined at its distal portion by the rigid rotating means 15a, and at its proximate portion by the distal portion of an obturator head seat and spring support 60 and at its sides by obturator head seat and spring support connector 62 which fixedly connects the obturator head seat and spring support 60 to the walls 10c of the valve compartment 10b. The spring means 64 is attached to the distal portion of the obturator head seat and spring support 60 and pushes against the rigid rotating means 15a.

Thus, the proximate portion 33a of the tubular member 9a is rotated in relation to the fixed distal portion 31a by rotation of the rigid rotating means 15a. In practice, the rotating means 15a is lifted against the force of the spring means 64 and away from the circular plate 12a and then rotated. As can be seen from FIGS. 15 and 16, the rotating means 15a extends out beyond the outermost wall of the obturator head seat and spring support connector 62 and is easily grasped for such lifting and rotating. A surgical instrument such as an obturator 21 is inserted through the valve assembly 7a and the rotating means 15a is rotated until the intermediate portion 32a forms an air-tight seal against the obturator shield 26. The rotating means 15a is released and the force exerted by the spring means 64 propels the pins 18a into the detent pin receiving means 13a and maintains the pins 18a in fixed position.

The detent pin receiving means 13a is disposed on the circular plate 12a of the valve compartment 10b. The individual detents making up the detent pin receiving means 13a may have varying degrees of depth. For example, FIG. 18 depicts shallow detents 13b and deeper detents 13c which accommodate different fixed settings of the valve assembly 7a. Thus, when maximum torsional force is applied, and the resilient tubular member 9a is at maximum twist, the tubular member 9a generates its maximum counter-torsional force. Therefore, the deeper detents 13c provide more holding surface area and are better suited to maintain the pins within the detents than are shallower detents 13b, which are better suited for resisting against the lower counter-torsional force generated when the tubular member 9a is at less than maximum twist. When the tubular member 9a is at maximum twist, the longitudinal length of the tubular member 9a is reduced by torsional compression. The deeper detents 13b also help accommodate the longitudinal change in orientation of the pins as the tube length decreases.

Figure 19:
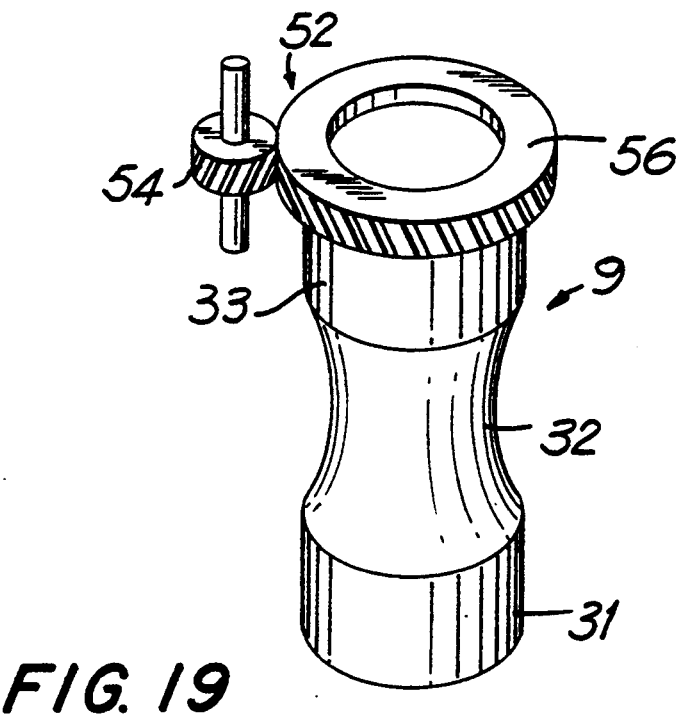
FIG. 19 is an isometric view of another embodiment of a portion of a variable dimension valve according to the present invention.

While the above-discussed valve assembly 7 and 7a incorporates a rotating means 15 and 15a and locking means 17 and 17a having a pin and detent mechanism to rotate and maintain diametral position, rotation of portions of the tubular member 9 and 9a may be controlled by a system of gears which imparts continuous diametral variability to the valve assembly. Thus, while the above-described pin and detent mechanisms maintain fixed, predefined diametral position, a gear mechanism allows a continuous range of diametral position to be achieved and maintained when desired. In FIG. 19, the tubular member 9 has affixed, at the proximate portion 33, involute helical gears 52 on parallel shafts. When first gear 54 is rotated, second gear 56 turns and causes the intermediate portion 32 to change diameter as above.

Figure 20:
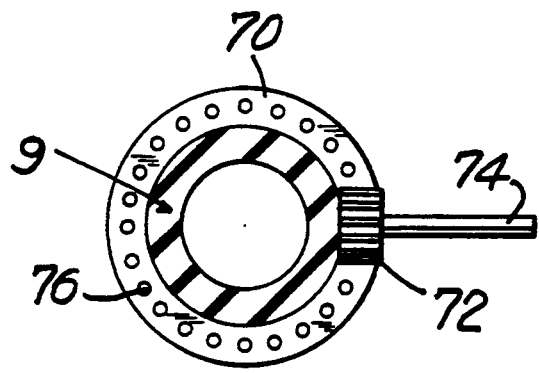
FIG. 20 is a top view of another embodiment of a portion of a variable dimension valve according to the present invention.
Figure 21:
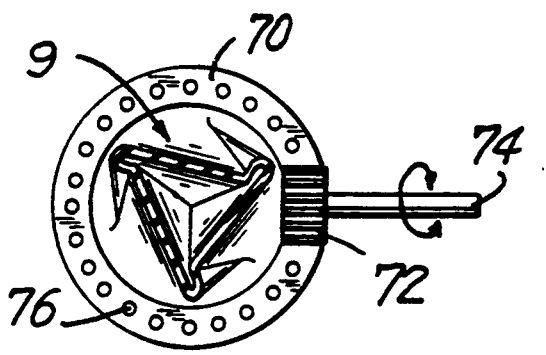
FIG. 21 is a top view of a portion of the variable dimension valve shown in FIG. 20, further depicting the valve part after a torsional force has been applied.

Another example of a suitable gear mechanism is illustrated in FIGS. 20 and 21. A pinwheel 70 having pins 76 is affixed to the proximate portion 33 of the tubular member 9, which pinwheel 70 communicates with a pinion gear 72. When shaft 74 attached to the pinion gear 72 is rotated, the pinwheel 70 rotates, thus rotating the proximate portion 33 in relation to the distal portion 31 and the interior dimension of the tubular member 9 is changed. FIG. 21 depicts the tubular member 9 as completely sealed after rotation of the pinion gear - pinwheel assembly. The gear assembly need not be restricted to the specific embodiments described above but can incorporate other gear assemblies that those with skill in the art might ordinarily use. In addition, the gear assembly can be automated, as in the case of a reversible electric motor which is attached to the gear assembly.

Although the illustrative embodiments of the present invention have been described herein with reference to the accompanying drawings, it is to be understood that the invention is not limited to those precise embodiments, and that various changes and modifications may be effected therein by one skilled in the art without departing from the scope or spirit of the invention.

What is claimed is:

1. A valve for selectively varying the inner opening of a cannula when positioned therein which comprises a generally tubular member having first and second end portions and a flexible intermediate portion, each end portion comprising a wall and said flexible intermediate portion comprising an intermediate wall, said intermediate wall being thinner than each said end portion wall, the boundary between at least one said end portion and said intermediate portion having a gradually tapered contour, wherein when said intermediate portion is subjected to torsional force the inner dimension of said intermediate portion changes.

2. A valve according to claim 1 wherein the torsional force is applied by rotating at least one of said first and second end portions in relation to said other.

3. A valve according to claim 2 wherein rotation of at least one of said first and second end portions in relation to said other causes a substantially air-tight seal to form between said intermediate portion and a surgical instrument disposed therein.

4. A valve according to claim 1 wherein at least said intermediate portion is resilient.

5. A valve according to claim 1 wherein the outer surface of said intermediate portion is fluted.

6. A valve according to claim 1 further comprising means for selectively fixing the dimension of the inner surface of said intermediate portion.

7. A valve according to claim 6 wherein said means for selectively fixing the dimension of the inner surface of said intermediate portion comprises a pinwheel and detent mechanism.

8. A valve according to claim 1 further comprising means for continuously varying and selectively fixing the dimension of the inner surface of said intermediate portion.

9. A valve according to claim 8 wherein said means for continuously varying and selectively fixing the dimension of the inner surface of said intermediate portion comprises a gear mechanism.

10. A valve according to claim 8 wherein said means for continuously varying and selectively fixing the dimension of the inner surface of said intermediate portion is automated.

11. A valve according to claim 1 wherein the outer surface of said intermediate portion is concave.

12. A variable interior dimension valve for use within a cannula assembly which comprises an elongated tubular member having an opening of generally cylindrical cross-section extending centrally therethrough, said tubular member having an intermediate portion thereof configured such that application of torsional force to the tubular member causes at least part of the intermediate portion to twist and vary the interior dimension of the intermediate portion, the intermediate portion comprising a wall which is thinner than walls of surrounding portions, the intermediate portion having at least one boundary which is gradually tapered into at least one of the surrounding portions.

13. A variable interior dimension valve according to claim 12 wherein the application of torsional force causes said portion to rotationally collapse and cause a reduction in the interior dimension of said portion.

14. A variable interior dimension valve according to claim 13 wherein said portion rotationally collapses in the form of a polygonal aperture.

15. A variable interior dimension valve according to claim 14 wherein the polygonal aperture is triangular.

16. A variable dimension valve for use within a cannula assembly comprising an elongated tubular member having an opening of generally cylindrical cross-section extending centrally therethrough, said tubular member having first and second end portions and a flexible intermediate portion of wall thickness less than each said end portion whereby application of torsional force to at least one end portion causes at least a portion of said intermediate portion to twist and vary the interior dimension of said intermediate portion.

17. A variable diameter valve according to claim 16 wherein said intermediate portion is resilient.

18. A variable diameter valve according to claim 16 wherein said intermediate portion is fluted.

* * * * *